United States Patent
Barbagli et al.

(10) Patent No.: US 10,478,162 B2
(45) Date of Patent: Nov. 19, 2019

(54) SYSTEMS AND METHODS FOR DISPLAY OF PATHOLOGICAL DATA IN AN IMAGE GUIDED PROCEDURE

(71) Applicant: INTUITIVE SURGICAL OPERATIONS, INC., Sunnyvale, CA (US)

(72) Inventors: Federico Barbagli, San Francisco, CA (US); Christopher R. Carlson, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 221 days.

(21) Appl. No.: 15/505,865

(22) PCT Filed: Aug. 20, 2015

(86) PCT No.: PCT/US2015/046078
§ 371 (c)(1),
(2) Date: Feb. 22, 2017

(87) PCT Pub. No.: WO2016/032846
PCT Pub. Date: Mar. 3, 2016

(65) Prior Publication Data
US 2017/0281139 A1    Oct. 5, 2017

Related U.S. Application Data

(60) Provisional application No. 62/041,040, filed on Aug. 23, 2014.

(51) Int. Cl.
*A61B 10/04* (2006.01)
*A61B 10/02* (2006.01)
(Continued)

(52) U.S. Cl.
CPC ............. *A61B 10/04* (2013.01); *A61B 1/01* (2013.01); *A61B 10/0233* (2013.01);
(Continued)

(58) Field of Classification Search
CPC ......... A61B 10/04; A61B 34/20; A61B 34/35; A61B 34/37; A61B 34/76; A61B 90/37;
(Continued)

(56) References Cited

U.S. PATENT DOCUMENTS

| 5,889,880 A | 3/1999 | Doerrer et al. |
| 6,380,732 B1 | 4/2002 | Gilboa |

(Continued)

FOREIGN PATENT DOCUMENTS

| JP | 2011524772 A | 9/2011 |
| JP | 2015518197 A | 6/2015 |

(Continued)

OTHER PUBLICATIONS

Extended European Search Report for Application No. EP15835684, dated Feb. 27, 2018, 7 pages.

(Continued)

*Primary Examiner* — Daniel L Cerioni
(74) *Attorney, Agent, or Firm* — Haynes & Boone, LLP (57) ABSTRACT

A method comprising: displaying, in a first region of a display screen, an image of a patient anatomy for guiding a medical instrument to a deployment location during a medical procedure; and recording a plurality of sample identifiers. Each sample identifier is associated with a corresponding tissue sample of a plurality of tissue samples. The method further includes recording a plurality of location stamps. Each location stamp indicates a location in the patient anatomy of a corresponding tissue sample of the plurality of tissue samples. The method further includes: receiving tissue sample pathology information for each (Continued)

tissue sample in the plurality of tissue samples; and displaying, in a table in a second region of the display screen, the plurality of sample identifiers, the plurality of location stamps, and the tissue sample pathology information for each tissue sample during the medical procedure.

26 Claims, 8 Drawing Sheets

(51) Int. Cl.
| | |
|---|---|
| *A61B 10/06* | (2006.01) |
| *A61B 34/20* | (2016.01) |
| *A61B 34/35* | (2016.01) |
| *A61B 34/37* | (2016.01) |
| *A61B 34/00* | (2016.01) |
| *A61B 90/00* | (2016.01) |
| *A61B 1/01* | (2006.01) |
| *A61B 17/00* | (2006.01) |
| *A61B 34/30* | (2016.01) |

(52) U.S. Cl.
CPC ........ *A61B 10/06* (2013.01); *A61B 17/00234* (2013.01); *A61B 34/20* (2016.02); *A61B 34/35* (2016.02); *A61B 34/37* (2016.02); *A61B 34/74* (2016.02); *A61B 34/76* (2016.02); *A61B 90/37* (2016.02); *A61B 2010/045* (2013.01); *A61B 2017/003* (2013.01); *A61B 2017/00203* (2013.01); *A61B 2017/00207* (2013.01); *A61B 2034/2055* (2016.02); *A61B 2034/2061* (2016.02); *A61B 2034/2065* (2016.02); *A61B 2034/256* (2016.02); *A61B 2034/301* (2016.02); *A61B 2034/741* (2016.02); *A61B 2034/742* (2016.02); *A61B 2090/364* (2016.02)

(58) Field of Classification Search
CPC ....... A61B 1/01; A61B 10/0233; A61B 10/06; A61B 7/00234
USPC ........................................................ 600/562
See application file for complete search history.

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 2003/0135115 | A1 | 7/2003 | Burdette et al. |
| 2006/0013523 | A1 | 1/2006 | Childlers et al. |
| 2011/0082363 | A1 | 4/2011 | Xu et al. |
| 2011/0137132 | A1 | 6/2011 | Gustafson |
| 2012/0071749 | A1 | 3/2012 | Xu et al. |
| 2012/0289777 | A1* | 11/2012 | Chopra .............. A61B 1/00009 600/109 |
| 2013/0006270 | A1* | 1/2013 | Schmoll ................ A61B 34/20 606/130 |
| 2013/0090554 | A1 | 4/2013 | Zvuloni et al. |
| 2013/0243302 | A1 | 9/2013 | Liu et al. |
| 2014/0018663 | A1 | 1/2014 | Harmer et al. |
| 2014/0098375 | A1* | 4/2014 | Liesener ............ G01B 9/02044 356/498 |
| 2014/0098376 | A1 | 4/2014 | Hashimshony et al. |
| 2015/0351860 | A1* | 12/2015 | Piron ................... A61B 5/0095 600/417 |
| 2016/0067007 | A1* | 3/2016 | Piron ................... A61B 5/7246 705/3 |

FOREIGN PATENT DOCUMENTS

| | | |
|---|---|---|
| WO | WO-2004019799 A2 | 3/2004 |
| WO | WO-2011161684 A2 | 12/2011 |

OTHER PUBLICATIONS

International Preliminary Report on Patentability for Application No. PCT/US2015/046078, dated Mar. 9, 2017, 9 pages.
International Search Report and Written Opinion for Application No. PCT/US2015/046078, dated Nov. 30, 2015, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR DISPLAY OF PATHOLOGICAL DATA IN AN IMAGE GUIDED PROCEDURE

RELATED APPLICATIONS

This patent application is the U.S. national phase of International Application No. PCT/US15/46078, filed Aug. 20, 2015, which designated the U.S. and claims priority to and the benefit of the filing date of U.S. Provisional Patent Application 62/041,040, entitled "SYSTEMS AND METHODS FOR DISPLAY OF PATHOLOGICAL DATA IN AN IMAGE GUIDED PROCEDURE," filed Aug. 23, 2014, each of which is incorporated by reference herein in its entirety.

FIELD

The present disclosure is directed to systems and methods for conducting an image guided procedure, and more particularly to systems and methods for displaying pathology data for tissue sampled during an image guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. These image-guided instruments may be tracked using, for example, electromagnetic (EM), mechanical, optical, or ultrasonic tracking systems. The image-guided instruments may navigate natural or surgically created passageways in anatomical systems such as the lungs, the colon, the intestines, the kidneys, the heart, the circulatory system, or the like. When image-guided medical instruments are used to remove tissue samples, the tissue samples are typically sent for analysis by a pathologist. The pathologist verbally communicates the results to the clinician. Systems and methods are needed to allow the clinician to receive additional information about the tissue samples that can be used to conduct further investigation, guide the acquisition of additional tissue samples, and/or improve procedure efficiency.

SUMMARY

The embodiments of the invention are summarized by the claims that follow the description.

In one embodiment, a method comprises displaying an image of a patient anatomy for guiding a medical instrument to a deployment location during a medical procedure. The method further comprises recording a first sample identifier for a first tissue sample and recording a second sample identifier for a second tissue sample. The method also comprises receiving first pathology information about the first tissue sample and receiving second pathology information about the second tissue sample. The method also comprises displaying the first sample identifier with the first pathology information during the medical procedure and displaying the second sample identifier with the second pathology information during the medical procedure.

In another embodiment, a system comprises a medical instrument including a catheter and a tool deployable from the catheter. The system also comprises a computer system configured to display an image of a patient anatomy for guiding a medical instrument to a deployment location during a medical procedure. The computer system is also configured to record a first sample identifier for a first tissue sample and record a second sample identifier for a second tissue sample. The computer system is also configured to receive first pathology information about the first tissue sample and receive second pathology information about the second tissue sample. The computer system is also configured to display the first sample identifier with the first pathology information during the medical procedure and display the second sample identifier with the second pathology information during the medical procedure.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
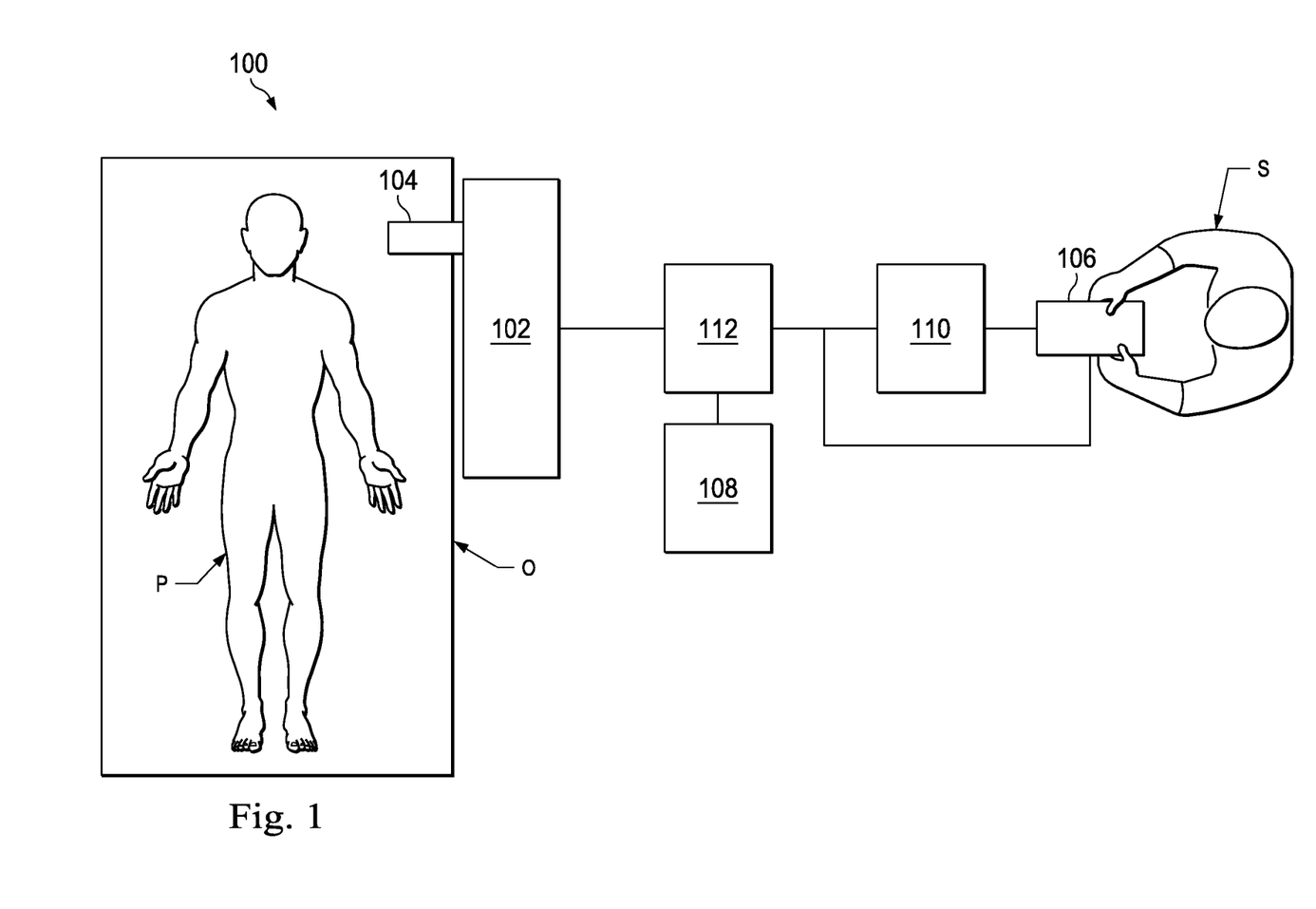
FIG. 1 is a teleoperated medical system, in accordance with embodiments of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a manipulator assembly 102 for operating a medical instrument 104 in performing various procedures on the patient P. The assembly 102 is mounted to or near an operating table O. A master assembly 106 allows the clinician or surgeon S to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments, the display 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided procedure. Virtual navigation using the virtual visualization system is based upon reference to the acquired preoperative or intraoperative dataset of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011)(disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
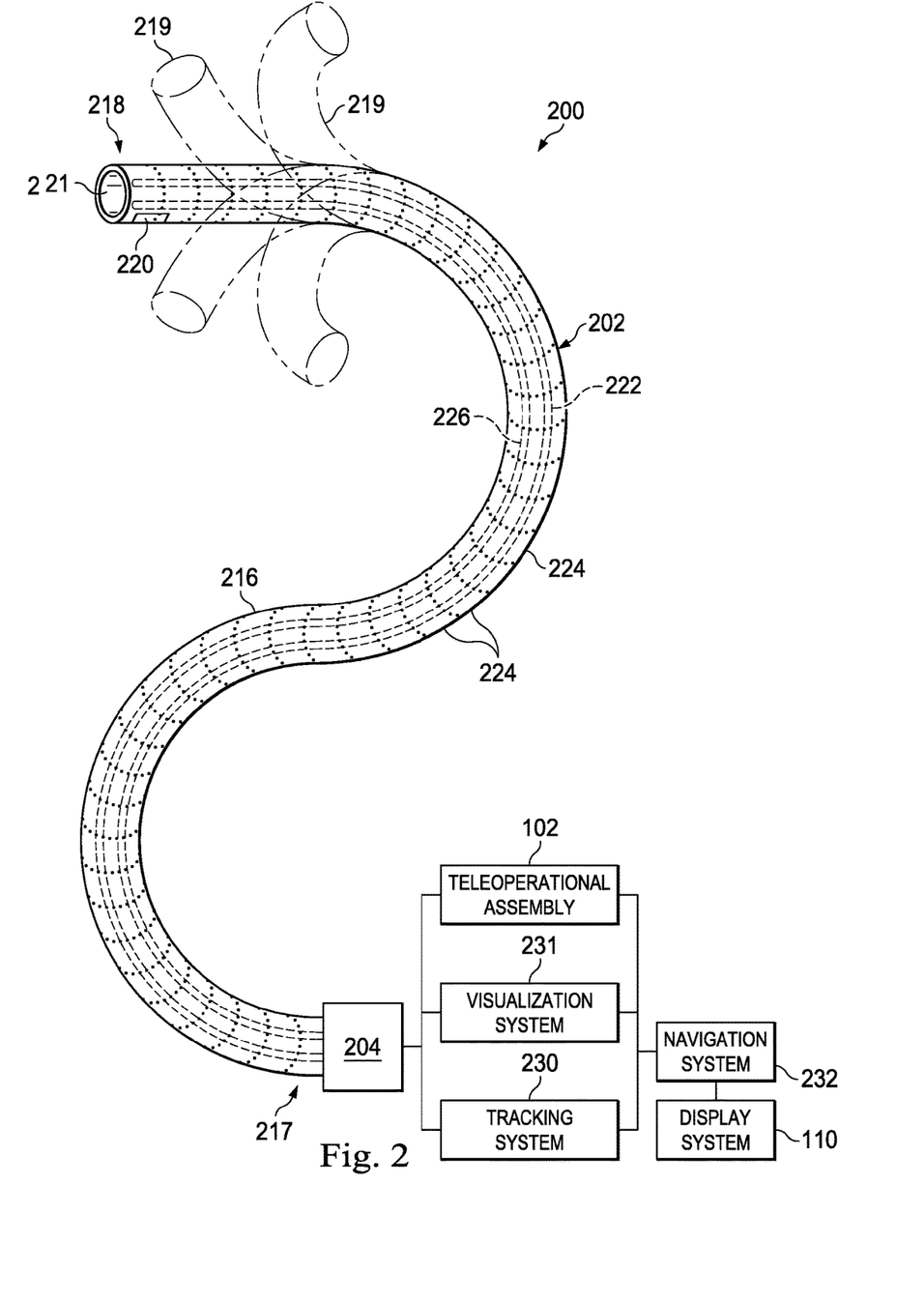
FIG. 2 illustrates a medical instrument system utilizing aspects of the present disclosure.

FIG. 2 illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figures 3, 4:
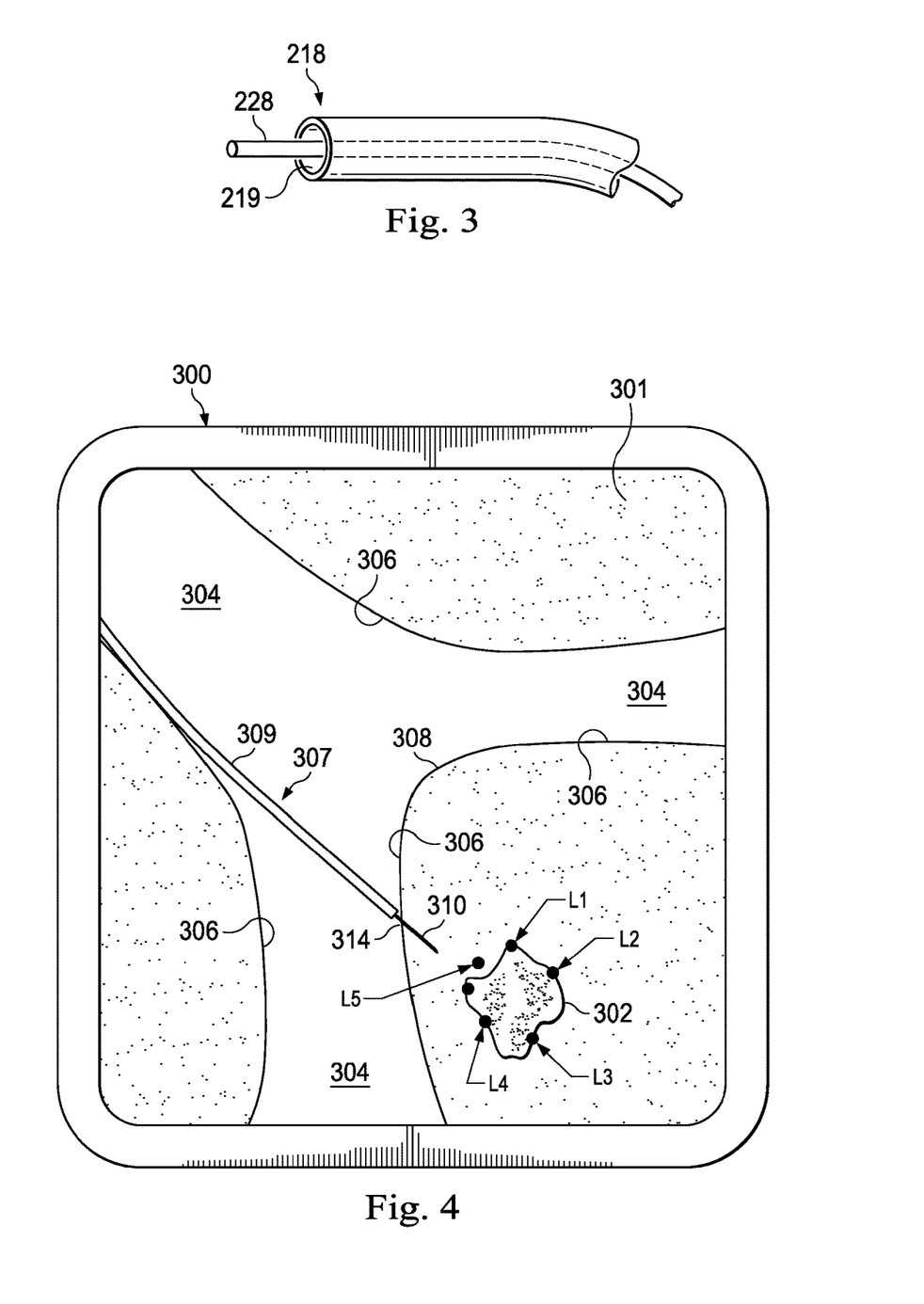
FIG. 3 illustrates a distal end of the medical instrument system of FIG. 2 with an extended medical tool.
FIG. 4 is a display screen providing a virtual image of a medical instrument in an anatomical region of a patient near a target location.

As shown in greater detail in FIG. 3, medical tool(s) 228 for such procedures as surgery, biopsy, ablation, illumination, irrigation, or suction can be deployed through the channel 221 of the flexible body 216 and used at a target location within the anatomy. If, for example, the tool 228 is a biopsy instrument, it may be used to remove sample tissue or a sampling of cells from a target anatomical location. The medical tool 228 may be used with an image capture probe also within the flexible body 216. Alternatively, the tool 228 may itself be the image capture probe. The tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

FIG. 4 illustrates a display screen 300 presenting a virtual image 301 from an anatomic model generated from a set of scanned images (e.g., pre-operative or intra-operative CT or MRI images). The virtual image 301 depicts a target structure 302, such as a tumor, and nearby anatomic passageways 304. The passageways include passageway walls 306 and carina 308. In this embodiment, the anatomic passageways are bronchial passageways of the lung, but the systems and methods of this disclosure may be suitable for use in other natural or surgically created passageways in anatomical systems such as the colon, the intestines, the kidneys, the heart, or the circulatory system.

The virtual image 301 further depicts an image of a medical instrument 307 (e.g., instrument 104, 200) registered with the image of the anatomy. The medical instrument 307 includes a flexible body 309 (substantially similar to flexible body 216) parked at a deployment location 314 with a medical tool 310 extended from the flexible body. The position and orientation of the image of the medical instrument 307 within a patient frame of reference may be determined based upon the previously described sensor systems. For example, the position, orientation, pose, and shape of the medical instrument and various points along the medical instrument, including the distal tip, may be localized in an anatomic frame of reference. As previously described, the location of a point such as the distal tip, in the anatomic frame, may be determined using EM sensors, fiber optic shape sensors, or fluoroscopic sensors. Other sensors for localizing the distal tip of the medical instrument may include ultrasound-based sensors, optical sensors, impedance based sensors, kinematic sensors, or a combination of any of these sensors. The image of the anatomy, including the anatomical model from which the image is obtained, is also registered to the anatomical frame of reference so that the image of the localized medical instrument (or at least of portion of the instrument) may be registered and co-displayed to generate the virtual image 301. The composite virtual image 301 thus indicates the location of the distal tip of the medical instrument within the lung. The view of the model and instrument may change, for example, to depict the lung in a state of inspiration or expiration. The instrument image may change to depict the advancement or withdrawal of the instrument through the bronchial passageways.

The medical tool 310 may be a biopsy tool for performing a biopsy procedure of the target structure 302. Tissue samples, including cell samples, may be gathered from the target structure 302 and/or the area around the target structure for removal through the flexible body 309. Multiple samples may be obtained from locations L1, L2, L3, L4, L5. With each sample, a sample identifier may be recorded. The sample identifier may include a location stamp indicating the location L1, L2, L3, L4, L5 from which the sample is obtained. The sample identifier may also or alternatively include a time stamp indicating a time at which or an order in which the sample occurred.

The removed samples may be prepared and analyzed by a pathology clinician such as a general pathologist, a histologist, or a cytologist. The pathology clinician determines histologic or cytologic information about the removed samples. Typically, the pathology clinician verbally communicates with the biopsy clinician, who obtained the samples, to convey histologic or cytologic information about the samples. This verbal communication may lead to confusion between the clinicians about which sample, of the multiple samples, the pathological information is describing. As will be described in detail below, clinician error may be reduced and procedure efficiency increased by displaying the histologic or cytologic information to the biopsy clinician via the display system.

Figure 5:
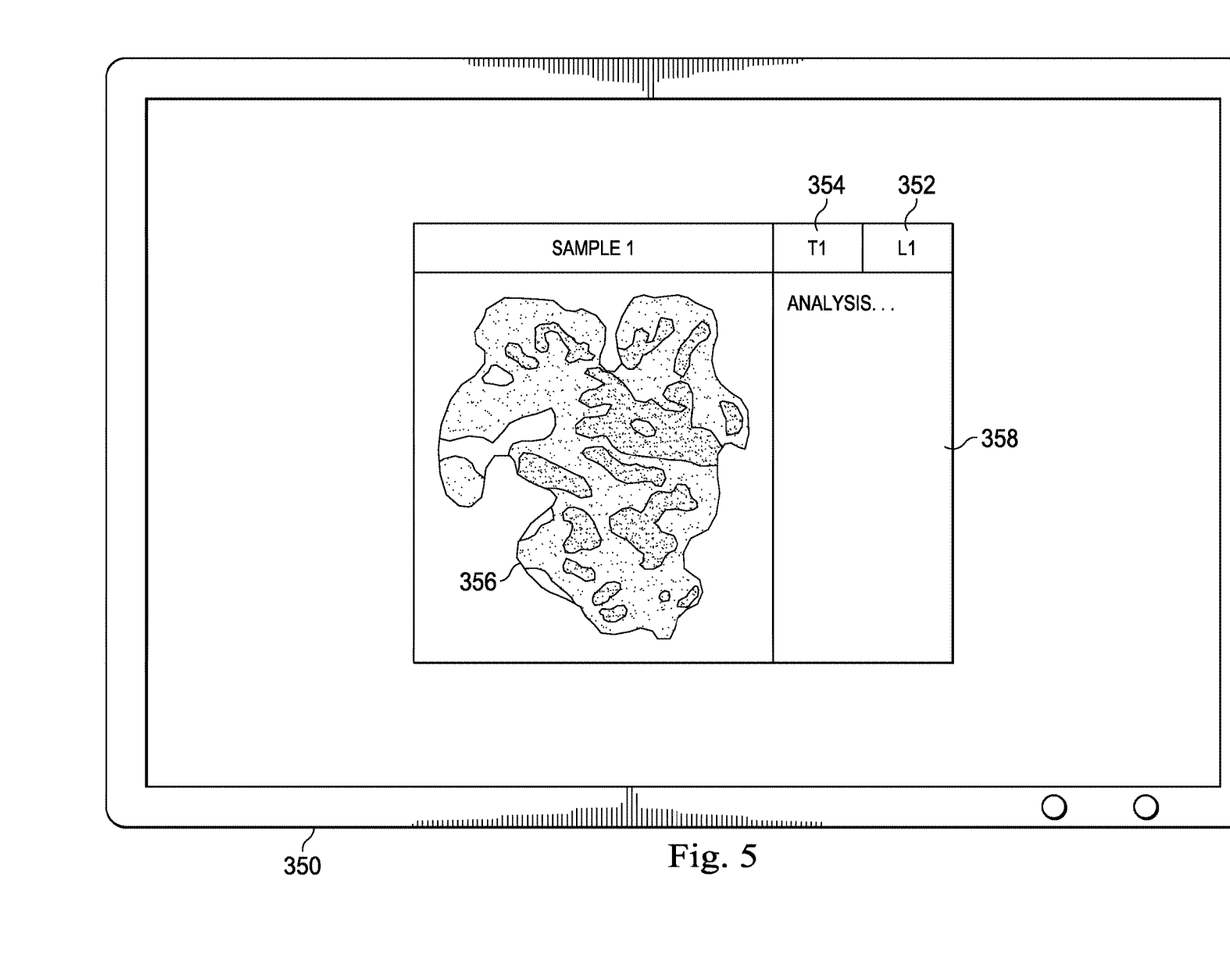
FIG. 5 illustrates a display providing pathologic information about a biopsy sample.

FIG. 5 illustrates a display 350 (e.g., the display 110) providing information about a biopsy Sample 1. Sample identifier information is presented including a location identifier 352 and a time identifier 354, both recorded when the sample was obtained. The sample identifier information is presented on a common display with an image 356 of the biopsied sample and with analytic information 358 about the Sample 1 provided by the analyzing pathologist. The analytic data may include, for example, a diagnosis, a description of the tissue or cells, or information about the apparent origin of the tumor. The image 356 of the biopsied sample and the histologic or cytologic analysis of the sample may be transmitted to the control system 112, via a wired or wireless communication interface, and may be displayed to the biopsy clinician while the image-guided procedure is in process. In some embodiments, the control system 112 may conduct further analysis using the images of the sampled tissue. For example, the control system 112 may conduct computational pathology analysis to compute histology and/or cytology based on image features and/or based on a database of prior cases. Computational pathology may be used to determine the etiology of the target tissue. This computed pathology information may also be presented to the biopsy clinician with the analytic information 358. After receiving the information, the biopsy clinician can determine whether additional samples are needed, in which location to take additional samples, and/or make a further evaluation of the sample. Because the sample identifier information is displayed with each set of sample analytics, the risk of confusing the results for multiple samples is reduced or eliminated.

Figure 6:
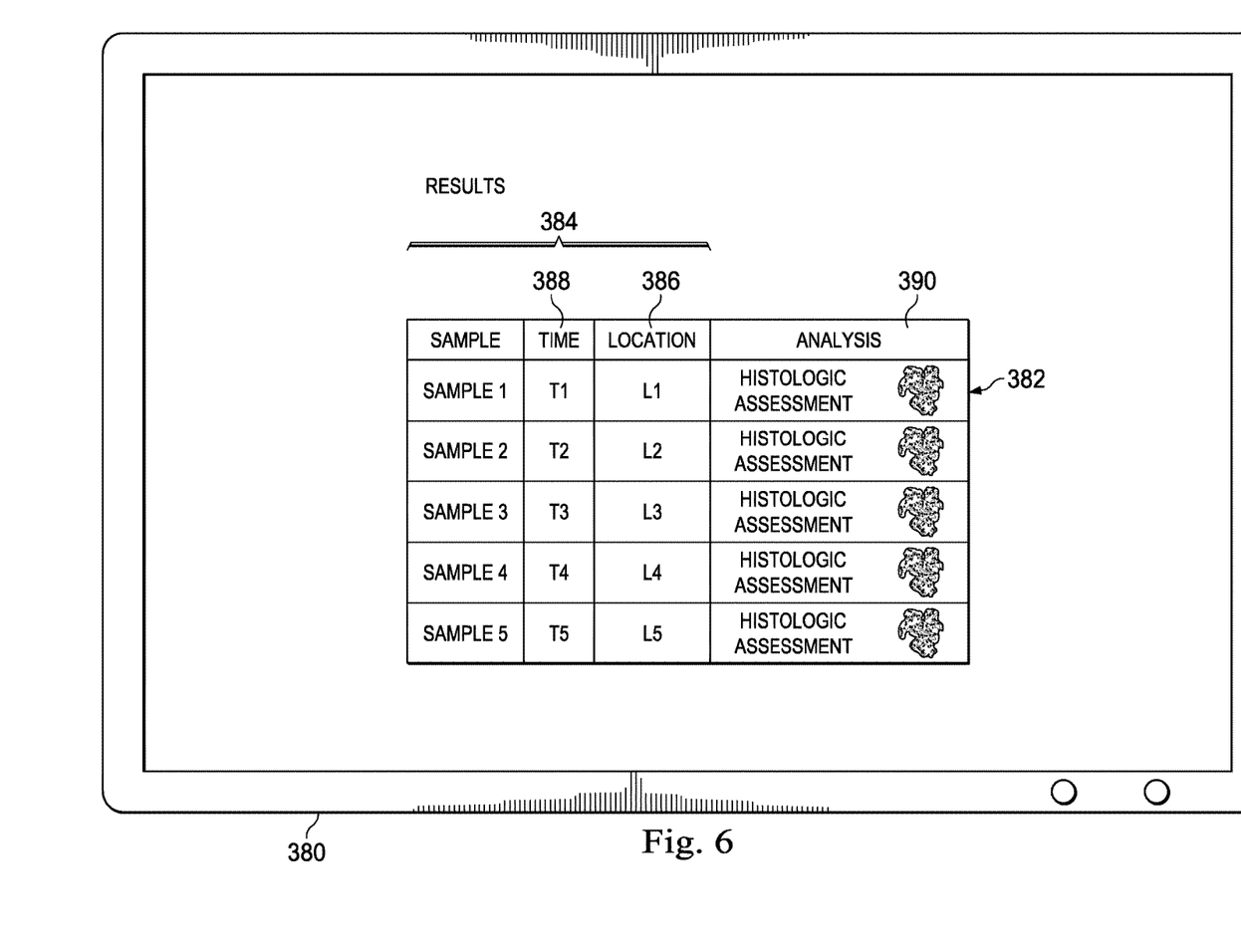
FIG. 6 illustrates a display with an image of a table for providing pathological data.

FIG. 6 illustrates a display 380 (e.g., the display 110) providing an image of a data table 382. The data table 382 provides information about multiples biopsy samples—Sample 1, Sample 2, Sample 3, Sample 4, Sample 5. For each sample, a sample identifier 384 includes a location identifier 386 and a time identifier 388. Each sample identifier is associated with pathologic information 390 (e.g. histologic and/or cytologic information) which may include images from a digital microscope and/or analytic data provided by a pathologist in the form of graphical information, drawings, text, numerical data. As described above, the analytic data may also include computational pathology results. The information for the table 382 may be transmitted to the control system 112, via a wired or wireless communication interface, and may be displayed to the biopsy clinician while the image-guided procedure is in process. In an alternative embodiment, the order of the pathologic information may serve as the sample identifier, indicating to the biopsy clinician the order in which the samples were obtained. In various alternatives, the images of the samples, the sample identifier information, and the analytics may be presented in a non-tabular format. Any logical arrangement of the information may be presented on a display. For example, the same information may be presented serially, with only one sample presented at a time. Alternatively, the sample information may be provided in response to the selection of biopsy locations (e.g., locations L1-L5) on an image guiding the medical procedure. For example, selecting location L1 causes the pathologic information (including any sample images) for the biopsy sample obtained from location L1 to be displayed alone or with the guiding image on a common display.

Figure 7:
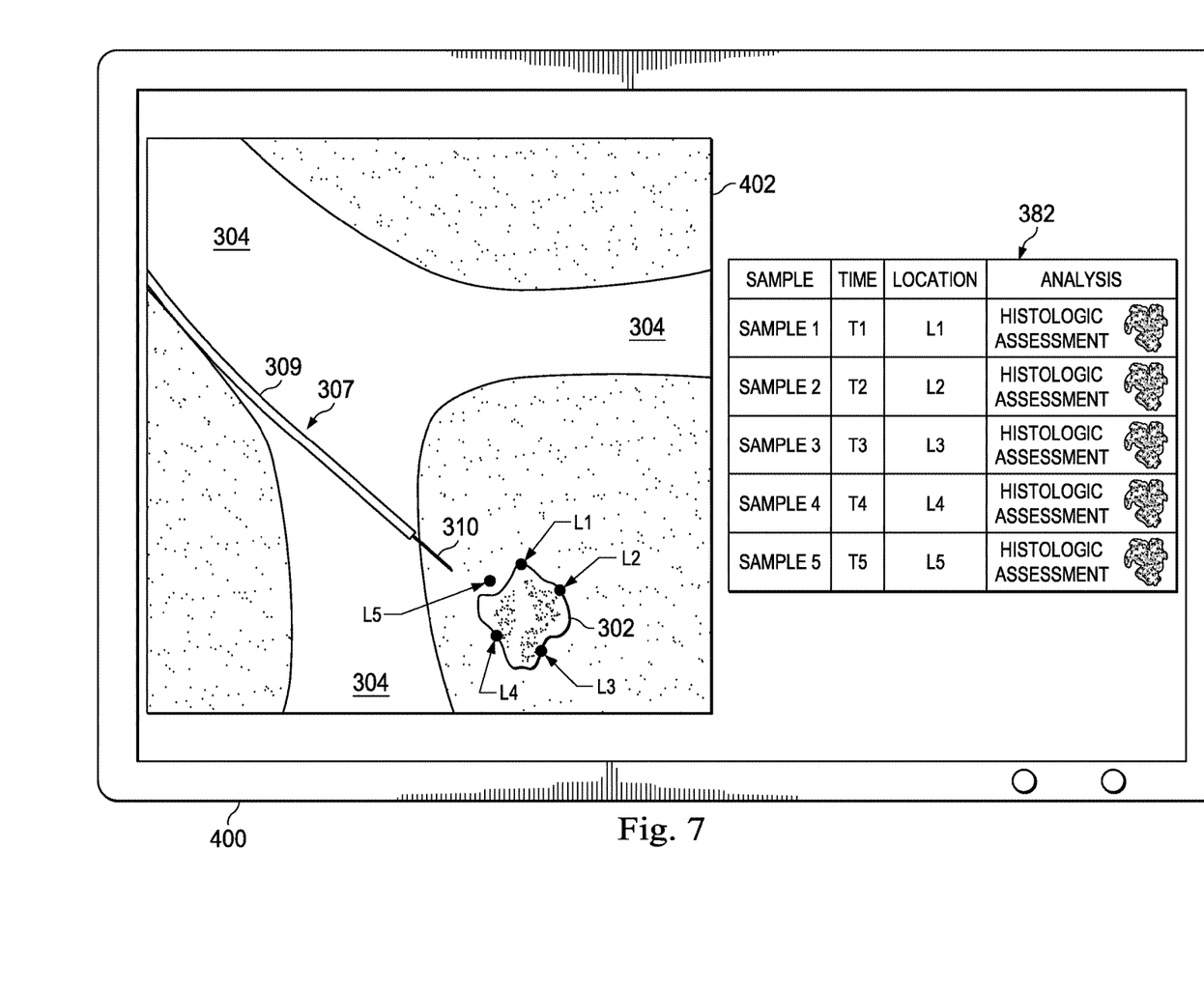
FIG. 7 illustrates a display screen providing pathological data in conjunction with a virtual image of the patient anatomy.

FIG. 7 illustrates a display 400 (e.g., the display 110) providing a real-time virtual image 402 of the medical instrument 307 superimposed or otherwise combined with an image obtained from preoperative or intraoperative imaging or modeling. On the same display 400, the data table 382 is provided. With the real-time virtual image 402 and the pathologic information for the samples presented on the same display while the image-guided medical procedure is in process, the biopsy clinician can determine whether additional samples are needed, in which location to take additional samples, and/or make a further evaluation of the sample. Because sample identifier information is provided with each set of sample analytics, the risk of confusing the results for multiple samples is reduced or eliminated. In some embodiments the sample identifier information or markers indicating the location of the samples may be displayed on the image 402, allowing the biopsy clinician to easily relate the fields in the table 382 with the biopsied locations in or near the target 302. Optionally, any of the markers mapping the location of the biopsies may be selected (e.g., with a mouse-click or other selection indicator) causing the pathological information about that particular location to be displayed to the biopsy clinician.

Figure 8:
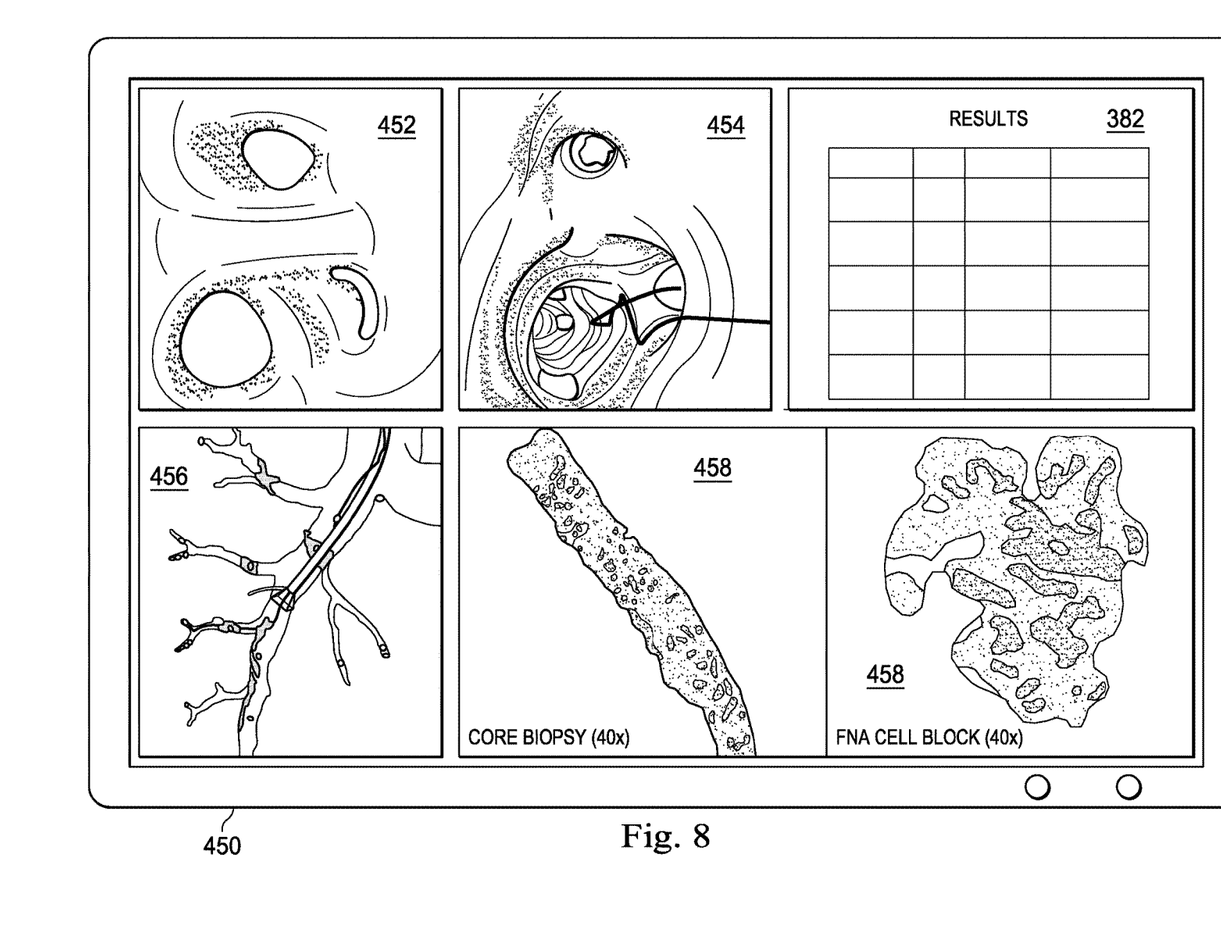
FIG. 8 is a display screen providing pathological data in conjunction with multiple images of the patient anatomy.

FIG. 8 illustrates another display 450 (e.g., the display 110) providing a full suite of guidance images for the biopsy clinician. The display 450 includes a real-time image 452 obtained from the visualization system 231 of the medical instrument (e.g., a real-time endoscopic image). The display 450 also includes a virtual internal anatomical image 454 (e.g., a "fly-through" view) obtained from pre-operative or intra-operative images. The image 454 is obtained from the perspective of the distal end of the medical instrument based on the sensed location and orientation of the distal end of the medical instrument. The display 450 also includes a virtual composite image 456 (e.g., an atlas image) presenting the medical instrument superimposed or otherwise combined with an image obtained from preoperative or intraoperative imaging or modeling. On the same display 450, the data table 382 or another format for providing pathologic information is provided. One or more images 458 of the sampled tissue may selected for display. The images 458 may be manipulated with zoom in/out capability, color adjustment, annotations, or the like. With the real-time images 402 452, 454, 456 and the pathologic information for the samples presented on the same display while the image-guided procedure is in process, the biopsy clinician can determine whether additional samples are needed, in which location to take additional samples, and/or make a further evaluation of the sample.

Figure 9:
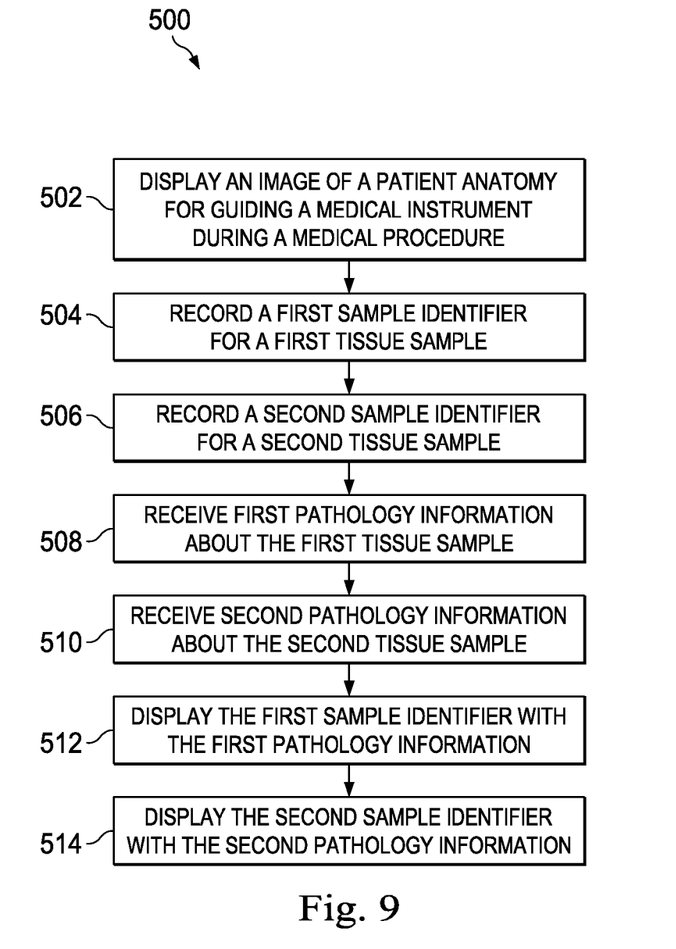
FIG. 9 is a flowchart describing a method for correlating pathological data with an image guided medical procedure.

FIG. 9 is a flowchart describing a method 500 for correlating pathologic information with an image-guided medical procedure. A process 502 includes displaying an image of the patient anatomy for guiding the medical instrument during a medical procedure such as a biopsy. As previously described, the image may be a two dimensional or three dimensional image obtained from pre-operative or intra-operative imaging. Using the displayed image for guidance, a biopsy clinician may obtain multiple tissue samples from a target area of the patient. At process 504, a first sample identifier is recorded for a first tissue sample. At process 506, a second sample identifier is recorded for a second tissue sample. The tissue samples are analyzed by a pathologist and/ or analyzed using computational pathology algorithms. At process 508, first pathology information about the first tissue sample is received. At process 510, second pathology information about the second tissue sample is received. The pathology information may be received via wired or wireless connection from a pathology clinician or may be received from a processor that performs computational pathology. At process 512, the first sample identifier is displayed in a common display with the first pathology information. At process 514, the second sample identifier is displayed in a common display with the second pathology information. For example, the first or second pathology information may be displayed together with the location and/or time at which the sample was obtained. At least one of the sets of pathology information, the corresponding sample identifier, and the image of the patient anatomy may be displayed together on a single display during the medical procedure. The displayed pathology information is provided to the biopsy clinician during the medical procedure (e.g., while the patient remains sedated or while the patient remains in the treatment area where the tissue samples were removed) so that the biopsy clinician may use the pathology information to determine if additional biopsies are needed and where those additional biopsies should occur. Because the pathology information is displayed during the same medical procedure in which the original biopsy samples were obtained, subsequent biopsies may be conducted without requiring a second medical procedure on the patient to conduct the additional biopsies.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
displaying, in a first region of a display screen, an image of a patient anatomy for guiding a medical instrument to a deployment location during a medical procedure;
recording a plurality of sample identifiers, wherein each sample identifier of the plurality of sample identifiers is associated with a corresponding tissue sample of a plurality of tissue samples;
recording a plurality of location stamps, wherein each location stamp of the plurality of location stamps indicates a location in the patient anatomy of a corresponding tissue sample of the plurality of tissue samples;
receiving tissue sample pathology information for each tissue sample in the plurality of tissue samples; and
displaying, in a table in a second region of the display screen, the plurality of sample identifiers, the plurality of location stamps, and the tissue sample pathology information for each tissue sample during the medical procedure.

2. The method of claim 1 further comprising:
receiving a first tissue sample of the plurality of tissue samples from the patient anatomy into the medical instrument.

3. The method of claim 1, wherein the image of the patient anatomy is captured by the medical instrument, and wherein the displaying of the tissue sample pathology information occurs while at least a portion of the medical instrument is contained within the patient anatomy.

4. The method of claim 1 wherein the image of the patient anatomy is a pre-operative image of the patient anatomy.

5. The method of claim 1 further comprising displaying, in the image of the patient anatomy, a first location stamp of the plurality of location stamps, wherein the first location stamp is displayed at a first tissue sample site.

6. The method of claim 1 wherein the tissue sample pathology information for a first tissue sample of the plurality of tissue samples includes a digital image of at least a portion of the first tissue sample obtained from a digital microscope.

7. The method of claim 1 wherein the tissue sample pathology information for a first tissue sample of the plurality of tissue samples includes an analysis of the first tissue sample.

8. The method of claim 1 wherein the image of the patient anatomy is a three-dimensional model of the patient anatomy.

9. The method of claim 1 further comprising performing a pathology analysis of a first tissue sample of the plurality of tissue samples.

10. A system comprising:
a medical instrument including a movable portion that is controlled using a computer system, the computer system including a processor and a memory,
wherein the memory includes machine readable instructions that, when executed by the processor, cause the system to:
display, in a first region of a display screen, an image of a patient anatomy for guiding the medical instrument to a deployment location during a medical procedure;
record a plurality of sample identifiers, wherein each sample identifier of the plurality of sample identifiers is associated with a corresponding tissue sample of a plurality of tissue samples;
record a plurality of location stamps, wherein each location stamp of the plurality of location stamps indicates a location in the patient anatomy of a corresponding tissue sample of the plurality of tissue samples;
receive tissue sample pathology information for each tissue sample in the plurality of tissue samples; and
display, in a table in a second region of the display screen, the plurality of sample identifiers, the plurality of location stamps, and the tissue sample pathology information for each tissue sample during the medical procedure.

11. The system of claim 10 wherein the memory further comprises machine readable instructions that, when executed by the processor, cause the system to receive a first tissue sample of the plurality of tissue samples from the patient anatomy into the medical instrument.

12. The system of claim 10 wherein the medical instrument includes an image capture system for capturing the image of the patient anatomy, and wherein displaying the plurality of sample identifiers with the tissue sample pathology information during the medical procedure comprises displaying the plurality of sample identifiers with the tissue sample pathology information while at least a portion of the medical instrument is contained within the patient anatomy.

13. The system of claim 10 wherein the image of the patient anatomy is a pre-operative image of the patient anatomy.

14. The system of claim 10 wherein the memory further comprises machine readable instructions that, when executed by the processor, cause the system to display, in the image of the patient anatomy, a first location stamp of the plurality of location stamps, wherein the first location stamp is displayed at a first tissue sample site.

15. The system of claim 10 wherein the tissue sample pathology information for a first tissue sample of the plurality of tissue samples includes a digital image of at least a portion of the first tissue sample obtained from a digital microscope.

16. The system of claim 10 wherein the tissue sample pathology information for a first tissue sample of the plurality of tissue samples includes a pathology analysis of the first tissue sample.

17. The system of claim 10 wherein the image of the patient anatomy is a three-dimensional model of the patient anatomy.

18. The system of claim 10 wherein the memory further comprises machine readable instructions that, when executed by the processor, cause the system to perform a pathology analysis of a first tissue sample of the plurality of tissue samples.

19. The method of claim 1, wherein the image of the patient anatomy is a virtual image of the patient anatomy from a perspective of a distal end of the medical instrument, and wherein a first sample identifier of the plurality of sample identifiers is displayed with the virtual image of the patient anatomy.

20. The method of claim 1, further comprising:
recording a plurality of time stamps, each time stamp of the plurality of time stamps associated with a corresponding location stamp of the plurality of location stamps; and
displaying the plurality of time stamps in the table,
wherein the plurality of sample identifiers, the plurality of location stamps, the plurality of time stamps, and the tissue sample pathology information for each tissue sample is displayed in chronological order in the table.

21. The method of claim 1 further comprising displaying, in the image of the patient anatomy, each location stamp of the plurality of location stamps.

22. The method of claim 21, wherein each location stamp is displayed at a tissue sample site for each tissue sample of the plurality of tissue samples, wherein each tissue sample site corresponds to a respective location stamp of the plurality of location stamps.

23. The method of claim 5, further comprising:
receiving a user input selecting the first location stamp; and
based on the received user input, displaying tissue sample pathology information for a first tissue sample of the plurality of tissue samples, the first tissue sample corresponding to the first tissue sample site.

24. The system of claim 10 wherein the memory further comprises machine readable instructions that, when executed by the processor, cause the system to:
record a plurality of time stamps, each time stamp of the plurality of time stamps associated with a corresponding location stamp of the plurality of location stamps; and
display the plurality of time stamps in the table,
wherein the plurality of sample identifiers, the plurality of location stamps, the plurality of time stamps, and the tissue sample pathology information for each tissue sample is displayed in chronological order in the table.

25. The system of claim 10 wherein the memory further comprises machine readable instructions that, when executed by the processor, cause the system to display, in the image of the patient anatomy, each location stamp of the plurality of location stamps.

26. The system of claim 14 wherein the memory further comprises machine readable instructions that, when executed by the processor, cause the system to:
receive a user input selecting the first location stamp; and
based on the received user input, display tissue sample pathology information for a first tissue sample of the plurality of tissue samples, the first tissue sample corresponding to the first tissue sample site.

* * * * *